(12) United States Patent
Liu

(10) Patent No.: US 10,842,967 B2
(45) Date of Patent: Nov. 24, 2020

(54) AUGMENTED REALITY THERAPY FOR TREATING MENTAL HEALTH AND DEVELOPMENTAL DISORDERS

(71) Applicant: IFGCure Holdings, LLC, Los Angeles, CA (US)

(72) Inventor: Stephen H. Liu, Los Angeles, CA (US)

( * ) Notice: Subject to any disclaimer, the term of this patent is extended or adjusted under 35 U.S.C. 154(b) by 0 days.

(21) Appl. No.: 16/224,778

(22) Filed: Dec. 18, 2018

(65) Prior Publication Data

US 2019/0184130 A1    Jun. 20, 2019

Related U.S. Application Data

(60) Provisional application No. 62/599,838, filed on Dec. 18, 2017.

(51) Int. Cl.
| | |
|---|---|
| G06T 19/00 | (2011.01) |
| A61M 21/00 | (2006.01) |
| G16H 20/70 | (2018.01) |
| G16H 40/60 | (2018.01) |
| G16H 80/00 | (2018.01) |
| G02B 27/01 | (2006.01) |

(52) U.S. Cl.
CPC .......... *A61M 21/00* (2013.01); *G06T 19/006* (2013.01); *G16H 20/70* (2018.01); *G16H 40/60* (2018.01); *G16H 80/00* (2018.01); *A61M 2021/005* (2013.01); *A61M 2021/0027* (2013.01); *A61M 2205/507* (2013.01); *G02B 2027/0178* (2013.01)

(58) Field of Classification Search
None
See application file for complete search history.

(56) References Cited

U.S. PATENT DOCUMENTS

| | | | |
|---|---|---|---|
| 5,722,418 | A | 3/1998 | Bro |
| 5,736,986 | A | 4/1998 | Sever, Jr. |
| 5,807,114 | A | 9/1998 | Hodges |
| 6,012,926 | A | 1/2000 | Hodges et al. |
| 6,057,846 | A | 5/2000 | Sever |
| 6,205,716 | B1 | 3/2001 | Peltz |
| 7,024,398 | B2 | 4/2006 | Kilgard |
| 9,576,106 | B2 | 2/2017 | Ahrnad |
| 9,585,616 | B2 | 3/2017 | Bowers et al. |
| 9,589,475 | B2 | 3/2017 | Lycas |
| 9,649,469 | B2 | 5/2017 | Hyde et al. |
| 9,694,155 | B2 | 7/2017 | Panova |
| 9,907,730 | B2 | 3/2018 | Macoviak |
| 9,978,288 | B2 | 5/2018 | Lok et al. |
| 10,013,531 | B2 | 7/2018 | Richards et al. |
| 2004/0197750 | A1 | 10/2004 | Donaher |
| 2005/0216243 | A1 | 9/2005 | Graham |

(Continued)

FOREIGN PATENT DOCUMENTS

WO    0062850    10/2000

*Primary Examiner* — Saptarshi Mazumder
(74) *Attorney, Agent, or Firm* — Ferguson Case Orr Paterson

(57) ABSTRACT

Methods and systems for using augmented reality (AR) technology in the mental health/developmental disorder treatment field. More particularly, methods and systems for providing a mental health/developmental disorder treatment service, process and system that introduces an input of a licensed healthcare professional into a patient's field of vision while he or she is utilizing a wearable medical device or wearable device.

19 Claims, 8 Drawing Sheets

(56) References Cited

U.S. PATENT DOCUMENTS

| | | |
|---|---|---|
| 2007/0027406 A1 | 2/2007 | LaPlaca et al. |
| 2007/0123757 A1 | 5/2007 | Chervinsky |
| 2007/0166690 A1 | 7/2007 | Johnson |
| 2008/0096665 A1 | 4/2008 | Cohen |
| 2008/0199841 A1 | 8/2008 | Aguilar-Long |
| 2008/0319252 A1 | 12/2008 | Chapman |
| 2010/0121156 A1 | 5/2010 | Yoo |
| 2011/0118555 A1 | 1/2011 | Han |
| 2011/0213197 A1 | 9/2011 | Robertson |
| 2011/0283203 A1 | 11/2011 | Periyannan et al. |
| 2012/0330869 A1 | 12/2012 | Durham |
| 2013/0246084 A1 | 9/2013 | Parmanto et al. |
| 2014/0058755 A1 | 2/2014 | Macoviak et al. |
| 2014/0222462 A1 | 8/2014 | Shakil et al. |
| 2014/0243608 A1 | 8/2014 | Hunt |
| 2014/0330576 A1 | 11/2014 | Bauer |
| 2015/0133812 A1 | 5/2015 | DeCharms |
| 2015/0174362 A1 | 6/2015 | Panova |
| 2015/0324532 A1* | 11/2015 | Jones .................. G06F 19/3418 705/2 |
| 2016/0026253 A1* | 1/2016 | Bradski ................ G02B 27/225 345/8 |
| 2016/0055307 A1* | 2/2016 | Macoviak ............. G06F 19/328 705/2 |
| 2016/0134640 A1 | 5/2016 | McCulloch |
| 2016/0155352 A1 | 6/2016 | Johnson |
| 2016/0246936 A1 | 8/2016 | Kahn |
| 2016/0317781 A1 | 11/2016 | Proud |
| 2017/0154159 A1 | 6/2017 | Rahman |
| 2017/0169177 A1 | 6/2017 | Beale et al. |
| 2017/0213006 A1 | 7/2017 | Beale et al. |
| 2017/0286617 A1 | 10/2017 | Zimmer |
| 2017/0319123 A1* | 11/2017 | Voss ....................... A61B 5/165 |
| 2017/0323485 A1 | 11/2017 | Samec et al. |
| 2018/0039752 A1 | 2/2018 | Subbarao |
| 2018/0120947 A1 | 5/2018 | Wells et al. |
| 2018/0121728 A1* | 5/2018 | Wells .................. A61B 5/0002 |
| 2018/0226158 A1 | 8/2018 | Fish et al. |
| 2018/0240353 A1* | 8/2018 | Bhuttar .................... G09B 9/00 |
| 2018/0268110 A1 | 9/2018 | Huynh |

* cited by examiner

AUGMENTED REALITY THERAPY FOR TREATING MENTAL HEALTH AND DEVELOPMENTAL DISORDERS

CROSS REFERENCE TO RELATED APPLICATIONS

This application claims the benefit of U.S. Provisional Application No. 62/599,838 entitled AUGMENTED REALITY THERAPY FOR TREATING MENTAL HEALTH AND DEVELOPMENTAL DISORDERS filed on Dec. 18, 2017, which is incorporated herein by reference in its entirety.

FIELD OF THE INVENTION

The present invention is directed to methods and systems for using augmented reality (AR) technology in the mental health developmental disorder field. More particularly, the present invention is directed to specifically treating mental health and developmental disorders, via processes and systems that introduces an input of a licensed healthcare professional, such as a therapist, into a patient's field of vision while he or she is utilizing a wearable medical device or wearable device.

BACKGROUND OF THE INVENTION

Mental health and developmental disorder problems are a serious worldwide issue, particularly in the United States. Often various groups of patients such as veterans, alcoholics, drug users, people with developmental disorders, and people undergoing excessive stress or family issues, require serious clinical intervention and support. While these issues can be physically influenced, often various issues stem from mental health disorders and can only be treated by receiving mental health treatment, typically by a licensed therapist.

Unfortunately, for many people suffering from mental health disorders, there are a lack of options for treatment. Specifically, there is a lack of easy access to be treated and it is often difficult for people suffering from mental health disorders to receive adequate treatment to diagnose and treat their mental disorders.

Such challenges involve having the person suffering from mental health disorders arrive at a therapist's office to receive a therapy treatment. In a typical therapy program, a patient visits a therapist at a hospital or clinic in order to be treated. However, this requires the patient to leave his or her home and to be checked into the hospital or clinic. For mental health patients, it is often difficult for them to arrive at a therapist's office to have their mental health disorders treated. For one, there is a strong social stigma associated with mental health that may dissuade individuals from seeking help in a public manner or visiting a therapist office. Often patients are reluctant to visit a therapist or healthcare professional in order to receive treatment, as such patients do not want to be seen by others seeking treatment or be perceived by the general public and friends as a 'mental case' of someone who needs help.

Second, patients suffering from mental health disorders often have difficulty adhering to a schedule and have difficulty remembering or attending therapy sessions.

Third, patients suffering from mental health disorders require treatment when they need it most, i.e., when they are in public high pressure environments, and often it is not possible to arrive at a therapist or healthcare professional's office to receive a treatment.

Alternatively, and recently, telehealth options have become available for patients. Telehealth involves the distribution of health-related services and information via electronic device and telecommunication technologies. Patients use electronic devices to communicate with licensed healthcare professionals, such as therapists, rather than going into an office.

Known systems and methods that use telehealth include US20040197750; US20050216243; US20070027406; US20070123757; US20070166690; US20080096665; US20080199841; US20080319252; US20100121156; US20110118555; US20110213197; US20110283203; US20120330869; US20130246084; US20140058755; US20140222462; US20140243608; US20140330576; US20150133812; US20150174362; US20160134840; US20160155352; US20160246936; US20160317781; US20170154159; US20170169177; US20170213006; US20170286617; US20170323485; US20180039752; US20180120947; US20180226158; US20180268110; U.S. Pat. Nos. 5,722,418; 5,736,986; 5,807,114; 6,012,926; 6,057,846; 6,205,716; 7,024,398; 9,576,106; 9,585,616; 9,589,475; 9,649,469; 9,694,155; 9,907,730; 9,978,288; U.S. Ser. No. 10/013,531; WO0062850A1.

However, despite the proliferation of telehealth technologies, individuals may lack a certain connection or sensory rapport when speaking to their licensed healthcare professional/therapist through an electronic device. Retention rates are also an issue, with patients often dropping out before completion of treatment using standard telehealth options.

These problems are exacerbated when dealing with patients having mental health, behavioral, or developmental disorder issues. These patients are extremely susceptible, have various issues, and often turn to drugs and other substances in order to solve their problems. Existing telehealth options are not geared towards mental health patients and there is no existing method or system that provides for an adequate solution to treat mental health disorders via telehealth.

Thus, it is an object of the present invention to improve upon present standard telehealth options and provide methods and systems that solve the problems set forth above, specifically for patients having mental health, behavioral and developmental disorders.

SUMMARY OF THE INVENTION

It is an object of the present invention to improve upon present standard telehealth options, specifically for patients having mental health, behavioral and developmental disorders.

The inventor of the application has researched various mental health issues, and has advantageously discovered using augmented reality (AR) to improve existing telehealth technologies, specifically for patients having mental health, behavioral and developmental disorders.

Thus, it is an object of the present invention to provide an augmented reality (AR) technology solution to overcome existing deficiencies in telehealth. It is an object of the present invention to provide an AR technology solution related to seeing a therapist, that replaces in-person and on-call visits for mental health disorder patients.

It is an object of the present invention to eliminate the need for a patient to travel to a hospital for mental health and developmental disorder treatment, and to protect the confidentiality of the patient so that he or she will not be stigmatized if seen in public. Also, by being more salient, stimulating, and non-threatening as well as providing comfort and accessibility in most locations—i.e. seeing a therapist projected out of your wearable medical device, such as an FDA approved device—patients are more likely to stick with the entire course of treatment. This can lead to increased engagement and lower no-show rates.

It is an object of the present invention to provide ease of use by removing the need to travel outside the home and by substituting handheld technology for wearable technology that may be used in a non-stigmatized fashion in most locations, public or private. This also means that patients can very likely be treated without public awareness, thus minimizing outside attention/scrutiny.

It is an object of the present invention to provide on-the-fly, on-demand treatment for patients, rather than having to go to a therapist office.

It is an object of the present invention to provide systems and methods of and for telehealth services whereby patients can interact with therapists in a non-office setting.

It is an object of the present invention for patients to put on either a wearable device or wearable medical device, which projects their therapist/licensed healthcare professional into their field of vision as a "life-like" figure that is able to interact and talk with them.

It is an object of the present invention for therapists and/or licensed healthcare professionals to treat mental health and developmental disorder problems using augmented reality.

These and other objects of the invention are achieved by providing a computer-implemented method for treating a patient suffering from a mental health, behavioral health, or developmental disorder using augmented reality (AR), the method comprising: providing an augmented reality (AR) device, the AR device having at least one processor; creating, via software executing on a processor, an AR field of view; overlaying, via software executing on a processor, an AR therapist within the AR field of view to create a modified AR field of view; and displaying the modified AR field of view on the AR device, wherein the AR therapist within the modified AR field of view provides a therapy to a patient to treat the patient suffering from a mental health, behavioral health, or developmental disorder.

In certain embodiments, the therapy is personalized to the patient.

In certain embodiments, the therapist is a live therapist.

In certain embodiments, the therapy is a recording of a therapist or a pre-recording of a therapist.

In certain embodiments, the field of view is a live field of view of the patient's current location or an alternative location.

In certain embodiments, the alternative location is selected from a group consisting of a beach, a bamboo forest, mountaintop of other location associated with relaxation.

In certain embodiments, the therapist engages in therapy conversation with the patient, specifically related to mental health, behavioral health, and developmental disorders.

In certain embodiments, disorders include anxiety disorders, mood disorders, schizophrenia and psychotic disorders, dementia, eating disorders.

In certain embodiments, the method is repeated until the treatment of the patient is completed. In certain embodiments, "completion" is a relative term and that patients may continue to lapse and that some treatment takes place for the patient's entire lifetime. In certain embodiments, completion occurs once a patient is treated for a mental health condition. In certain embodiments, the method is repeated until the patient completes a prescribed treatment plan.

In certain embodiments, the therapist actively treats the patient, such that the patient is able to ask questions to the therapist and have an interactive live conversation with the therapist.

In certain embodiments, the method allows for a connected network between patients and therapists, whereby patients are able to seamlessly choose between different therapist options to call into their field of view and therapists are able to seamlessly respond to the patients requesting this type of AR treatment and accept said requests, thus creating a unified patient/therapist network that matches up needed treatment with available treatment options.

Other objects of the invention are achieved by providing a connected network for treating patients suffering from a mental health, behavioral health, or developmental disorder using augmented reality (AR), the connected network comprising: at least one augmented reality device configured to perform a computer-implemented method as described herein, a server, and a therapist portal, wherein the connected network allows for at least one patient to use at least one augmented reality device to interact with at least one therapist, wherein whereby patients are able to seamlessly choose between different therapist options to call into their field of view and therapists are able to seamlessly respond to the patients requesting this type of AR treatment and accept said requests, thus creating a unified patient/therapist network that matches up needed treatment with available treatment options.

Other objects of the invention are achieved by providing an augmented reality (AR) device for treating a patient suffering from a mental health, behavioral health, or developmental disorder, comprising: at least one processor; at least one computer-readable storage media storing instructions which, when executed by the at least one processor: creates an AR field of view, overlays an AR therapist within the AR field of view to create a modified AR field of view, and displays modified AR field of view on the AR device, wherein the AR therapist within the modified AR field of view provides a therapy to a patient to treat the patient suffering from a mental health, behavioral health, or developmental disorder.

In certain embodiments, the AR device performs the methods listed herein.

In certain embodiments, the therapist actively treats the patient, such that the patient is able to ask questions to the therapist and have an interactive live conversation with the therapist using the device.

In certain embodiments, the device is either a wearable device or a wearable medical device.

In certain embodiments, the device is wirelessly connected to a computer or mobile phone.

In certain embodiments, the device is a stand-along device and is not connected to a computer or mobile phone.

In certain embodiments, the device is a headset. In certain embodiments, the device is a piece of glasses wear or an augmented reality headset.

In certain embodiments, the device is a head-mounted virtual retinal display.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
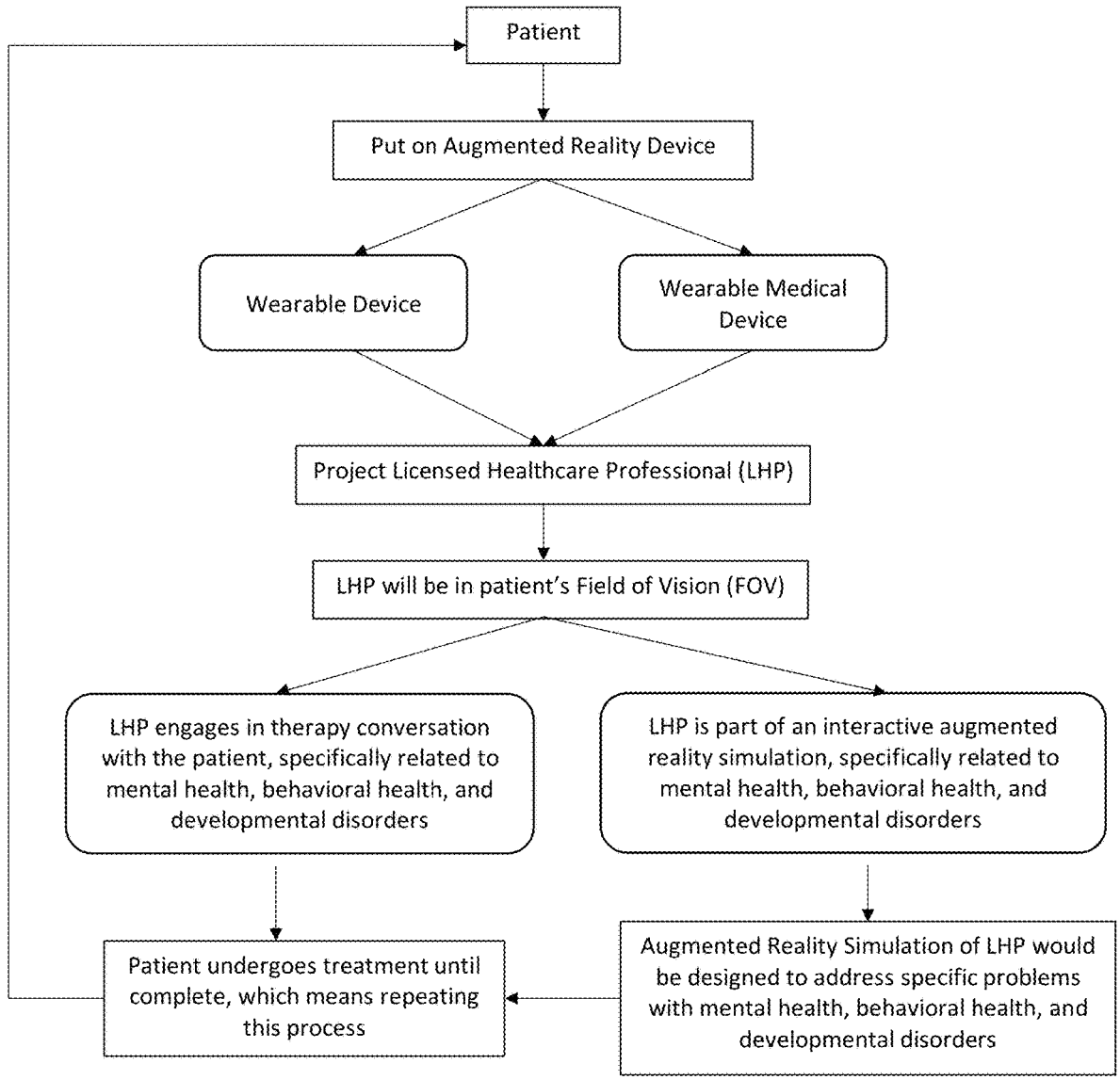
FIG. 1 is a flowchart detailing an embodiment of the present invention of a patient being treated for mental health and/or developmental disorders using an augmented reality (AR) device that projects a therapist and/or licensed healthcare professional into the patient's field of vision.

In the following description, numerous details are set forth for the purpose of explanation. However, one of ordinary skill in the art will realize that the invention may be practiced without the use of these specific details.

The invention is now described with reference to the drawings, wherein like reference numerals are used to refer to like elements throughout. In the following description, for purposes of explanation, numerous specific details are set forth in order to provide a thorough understanding of the subject invention. It may be evident, however, that the invention can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Augmented Reality

Augmented reality (AR) is an interactive experience of a real-world environment where the objects that reside in the real-world are "augmented" by computer-generated perceptual information, sometimes across multiple sensory modalities, including visual, auditory, haptic, somatosensory, and olfactory.

AR is something different from merely a multimedia system or an interactive computer graphics display. AR involves augmenting a user's vision to introduce or overlay an element. The overlaid sensory information can be constructive (i.e. additive to the natural environment) or destructive (i.e. masking of the natural environment) and is seamlessly interwoven with the physical world such that it is perceived as an immersive aspect of the real environment. In this way, augmented reality alters one's ongoing perception of a real world environment. Augmented reality is related to two largely synonymous terms: mixed reality and computer-mediated reality. The primary value of augmented reality is that it brings components of the digital world into a person's perception of the real world, and does so not as a simple display of data, but through the integration of immersive sensations that are perceived as natural parts of an environment.

Embodiments of the Invention

In embodiments of the invention, systems and methods are provided whereby a patient uses an augmented reality (AR) capable device that can either be a wearable device or a wearable medical device. In certain embodiments, the AR-capable device is wirelessly connected to a computer, mobile phone, or similar functioning apparatus that gives the device the capability to project augmented/mixed reality images, namely a therapist or licensed healthcare professional with the capability to interact and speak either through or as the projected image. In certain embodiments, the device has this same projection capability already built in, i.e. the operating system is built into the wearable device/wearable medical device.

In certain embodiments, a patient may also wear an auditory method that may or may not be built into the AR capable device.

In certain embodiments, the AR capable device projects out an augmented version of a licensed healthcare professional and/or therapist that is in the patient's field of vision. The patient is able to see the same space before and after using the AR device, while the input of the therapist is anchored to the real world through a projected image.

In certain embodiments, the projection can be used in private or public places, i.e. airplanes, crowded streets, at home. The licensed healthcare professional/therapist is able to interact, via the projection, with the patient in order to alleviate mental health problems or developmental disorders. This interaction will be an experience that is the equivalent of a therapy session or treatment.

In certain embodiments, the patient will undergo as many "therapy" or treatment sessions as necessary until the patient prescribed treatment plan is complete.

In certain embodiments, the invention involves having a therapist be projected using AR for live treatment that is accessible outside of the hospital system. This accessibility improves treatment methods for both patients and therapists.

Advantages and Long Felt Need

Using AR, therapists are able to treat a wider variety of patients because they can now form a close relationship with patients outside of their proximity as well as reduce downtime in-between seeing patients. Therapists can also treat patients from the comfort of their own home.

Using AR, the benefits for mental health patients are even greater. Patients are able to receive treatment anywhere, reducing the friction of carving time out of their day to see a therapist (driving, waiting in the lobby, etc.). This also addresses the social stigma of the perception of seeing a therapist, as patients can get treatment in public and no one will know, since the AR projection will only be able to be viewed by the one wearing the AR device.

Additionally, an AR projection of a therapist is able to connect both sides of a therapy session in a more seamless, efficient, and effective way.

Additional embodiments include providing treatment in emergency situations for a mentally disturbed patient whereby an AR therapist can intervene for life saving purposes for the patient or those around the patient.

Other embodiments are directed to providing tele-health in remote areas for stress management or mental health management.

Figures

Figure 2:
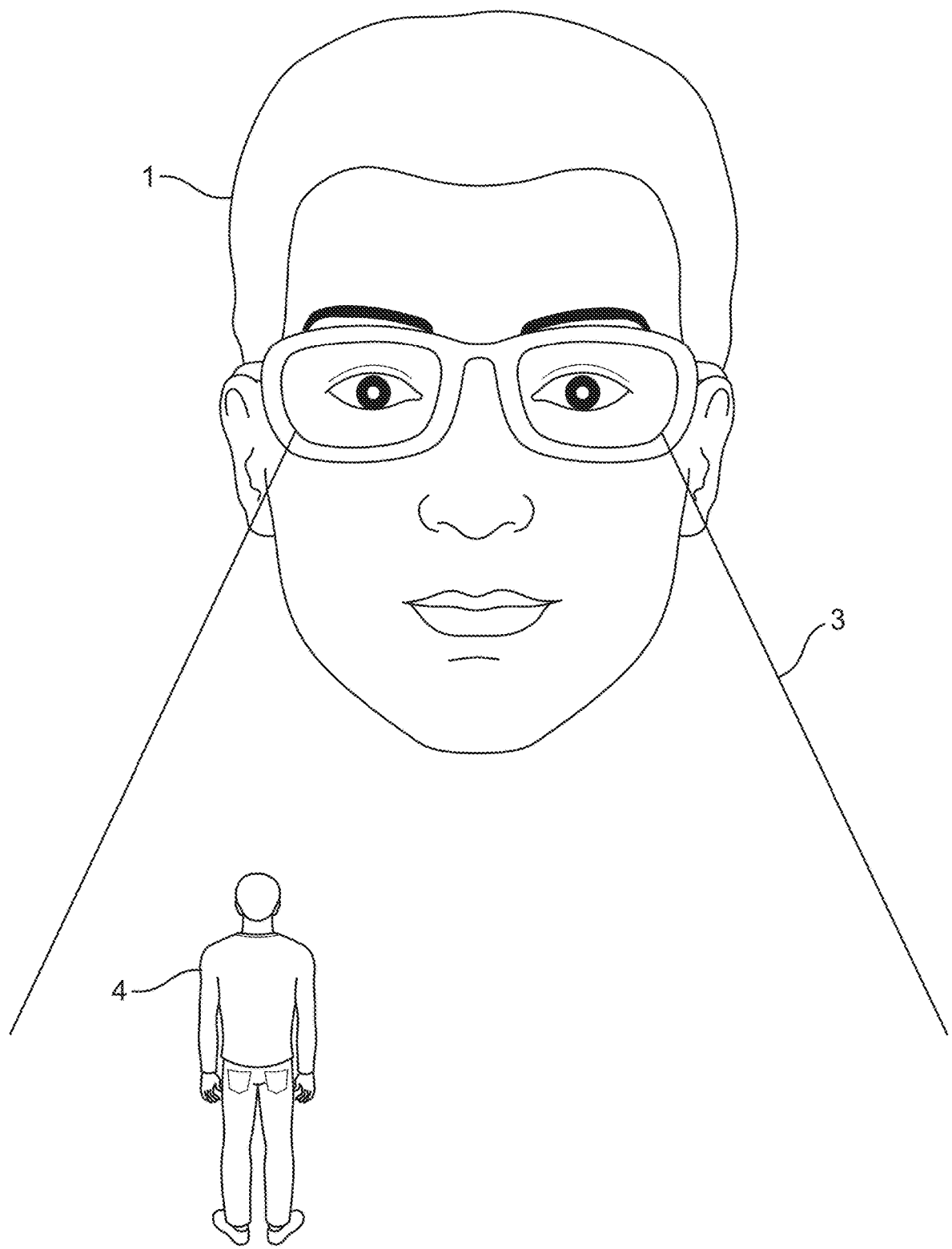
FIG. 2 depicts a patient's field of vision (3) when using a wearable device (1) for the specific purpose of treatment. As shown, element (4) is the licensed healthcare professional that the patient sees when the device is being born.
Figure 4:
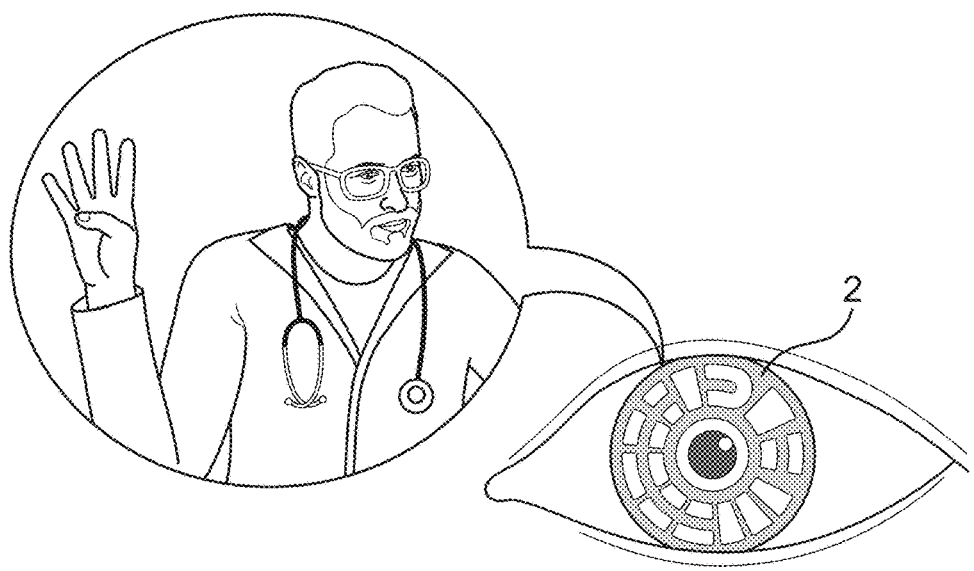
FIG. 4 depicts an embodiment of the present invention showing an up-close version of FIG. 3, detailing a wearable medical device (2) projecting the licensed healthcare professional (4).
Figure 3:
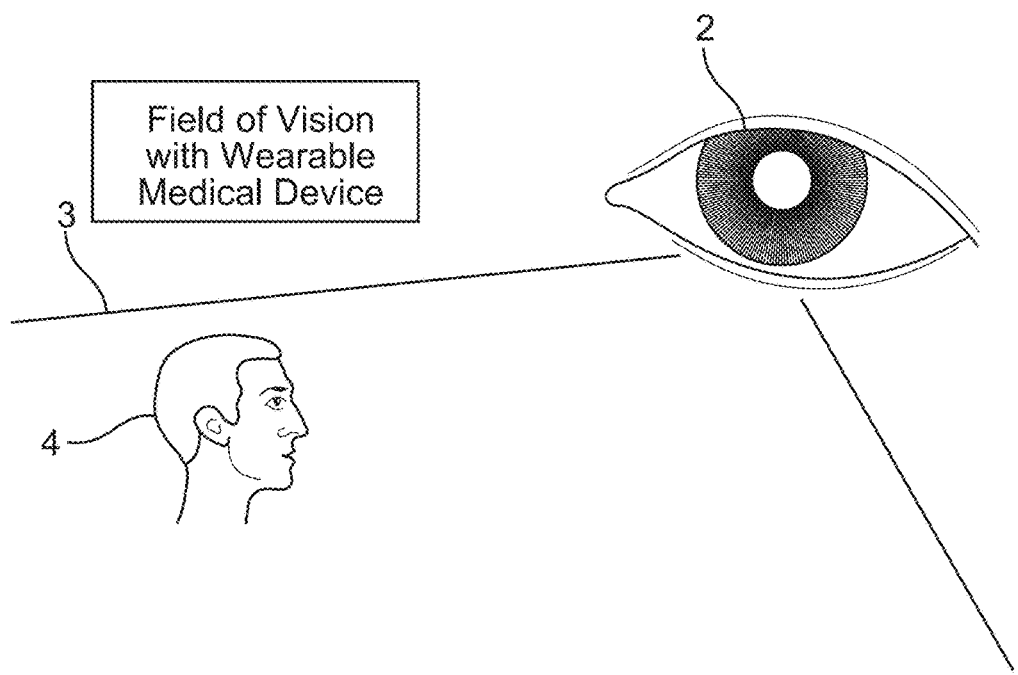
FIG. 3 depicts an embodiment of the present invention showing a patient's field of vision (3) when using a wearable medical device (2) for the specific purpose of treatment.

Referring to the figures, a patient starts by putting on an augmented reality (AR) capable device that can either be a wearable device (FIG. 2, (1)) or a wearable medical device (FIG. 3 and FIG. 4, (2)). This AR-capable device may be wirelessly connected to a computer, mobile phone, or similar functioning smart-device apparatus that gives the AR-capable device the capability to project augmented/mixed reality images, namely a therapist or licensed healthcare professional with the capability to interact and speak either through or as the projected image. It is contemplated that the device has this same projection capability already built in. The patient may also wear an auditory system that may or may not be built into the AR capable device.

Figure 5:
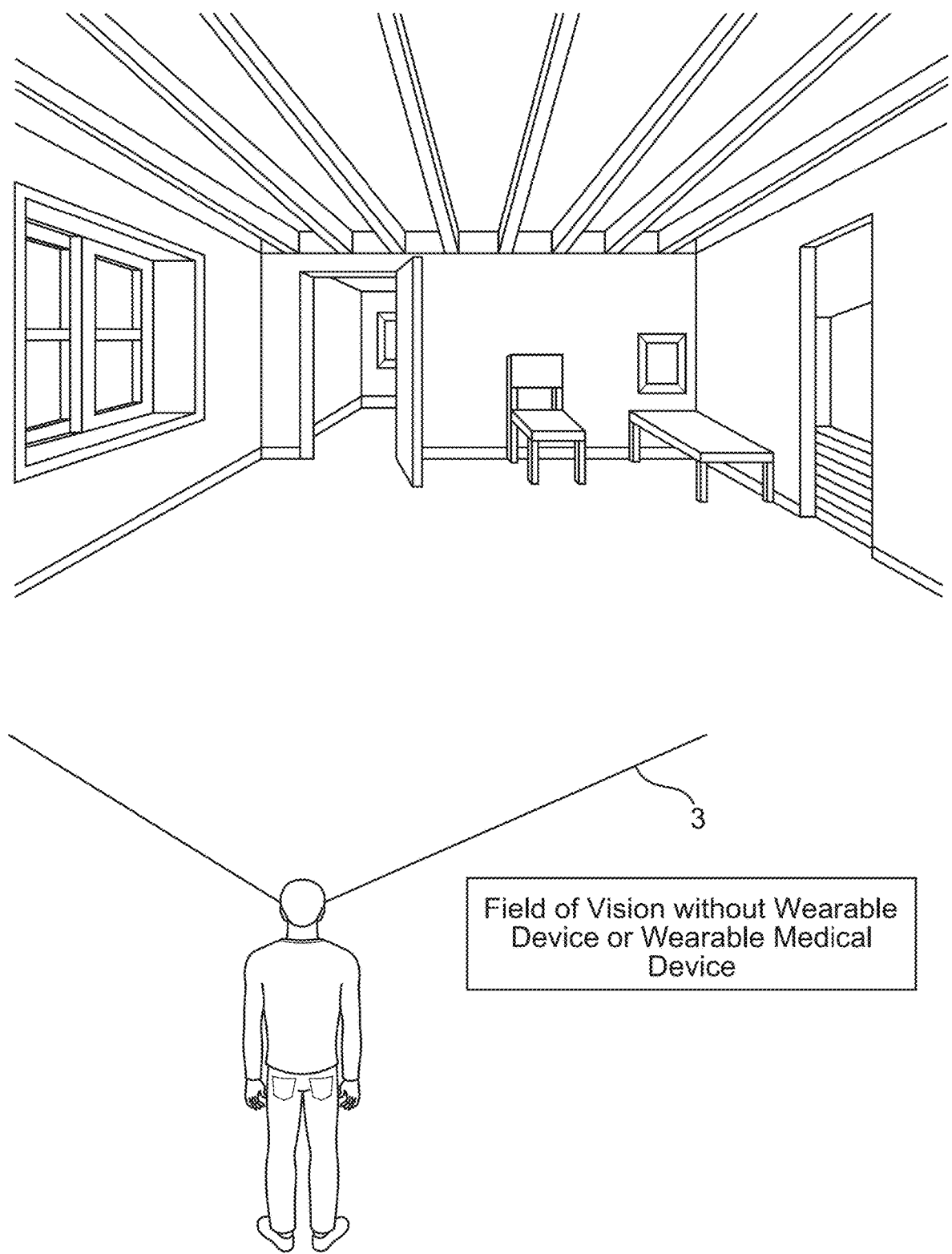
FIG. 5 depicts an embodiment of the present invention showing a patient's field of vision (3) before wearing any sort of wearable device or wearable medical device.
Figure 6:
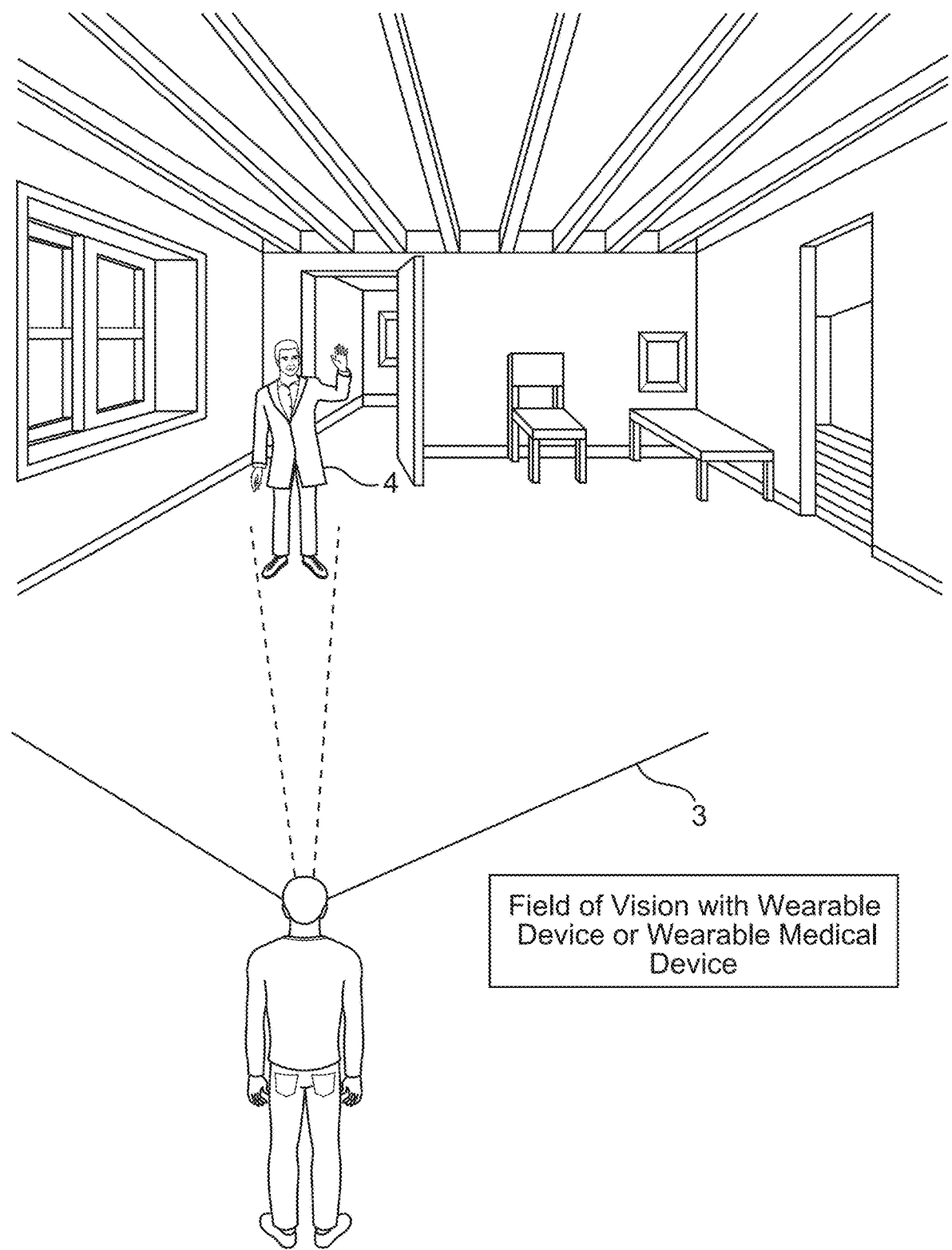
FIG. 6 depicts an embodiment of the present invention showing a patient's field of vision (3) while wearing a wearable device or a wearable medical device (1, 2) with a licensed healthcare professional (4) in view.

The AR capable device may project an augmented version of a licensed healthcare professional/therapist (FIG. 2, FIG. 3, and FIG. 6 (4)) that is in the patient's field of vision (FIG. 2, FIG. 3, FIG. 5 FIG. 6 (3)). As can be seen in FIG. 5 and FIG. 6, the patient may be able to see the same space before and after using the AR device, while the input of the therapist is anchored to the real world through a projected image. This projection can be used in private or public places i.e. airplanes, crowded streets, or at home. The licensed healthcare professional/therapist can interact, via the projection, with the patient in order to alleviate mental health problems or developmental disorders. This interaction and experience is the equivalent of a therapy session or treatment. The patient will undergo as many "therapy" or treatment sessions as necessary until treatment is complete.

Figure 7:
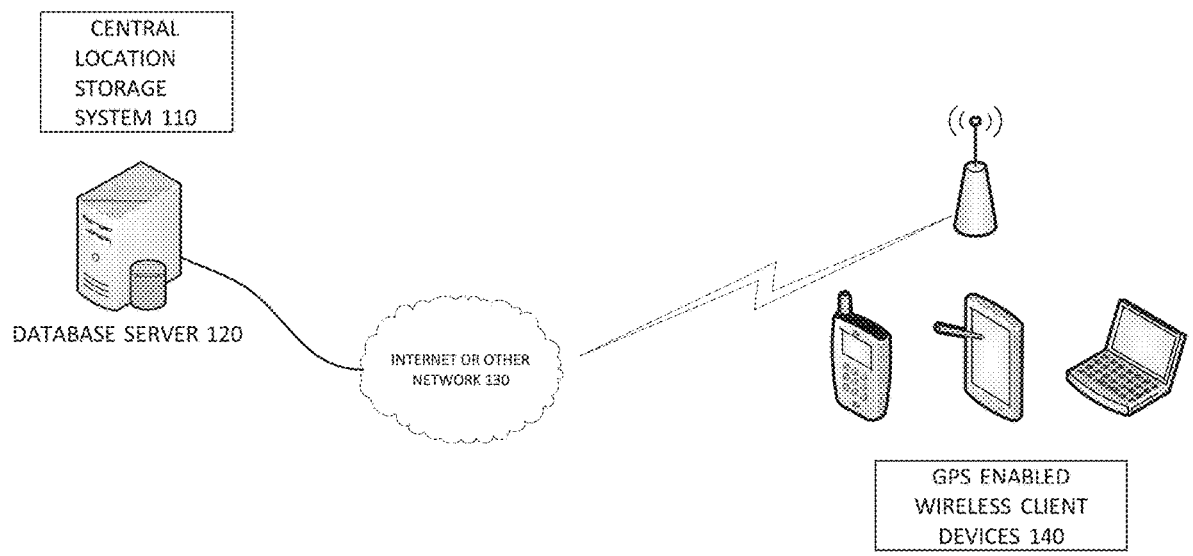
FIG. 7 is a schematic diagram of one embodiment of a system that can be used to practice aspects of the present invention.

FIG. 7 shows a schematic diagram of one embodiment of a system that can be used to practice aspects of the present invention. The schematic shows a central location storage system 110 and database server 120, which are connected to augmented reality devices 140 via the internet or other network 130. In this manner, augmented reality devices 140 can communicate with the database server 120 via the internet or other network 130. This allows a augmented reality devices to be located remote from the server, such that the augmented reality devices can be located at an remote from the server and from a therapist who is using a device that is communication with the augmented reality devices.

Figure 8:
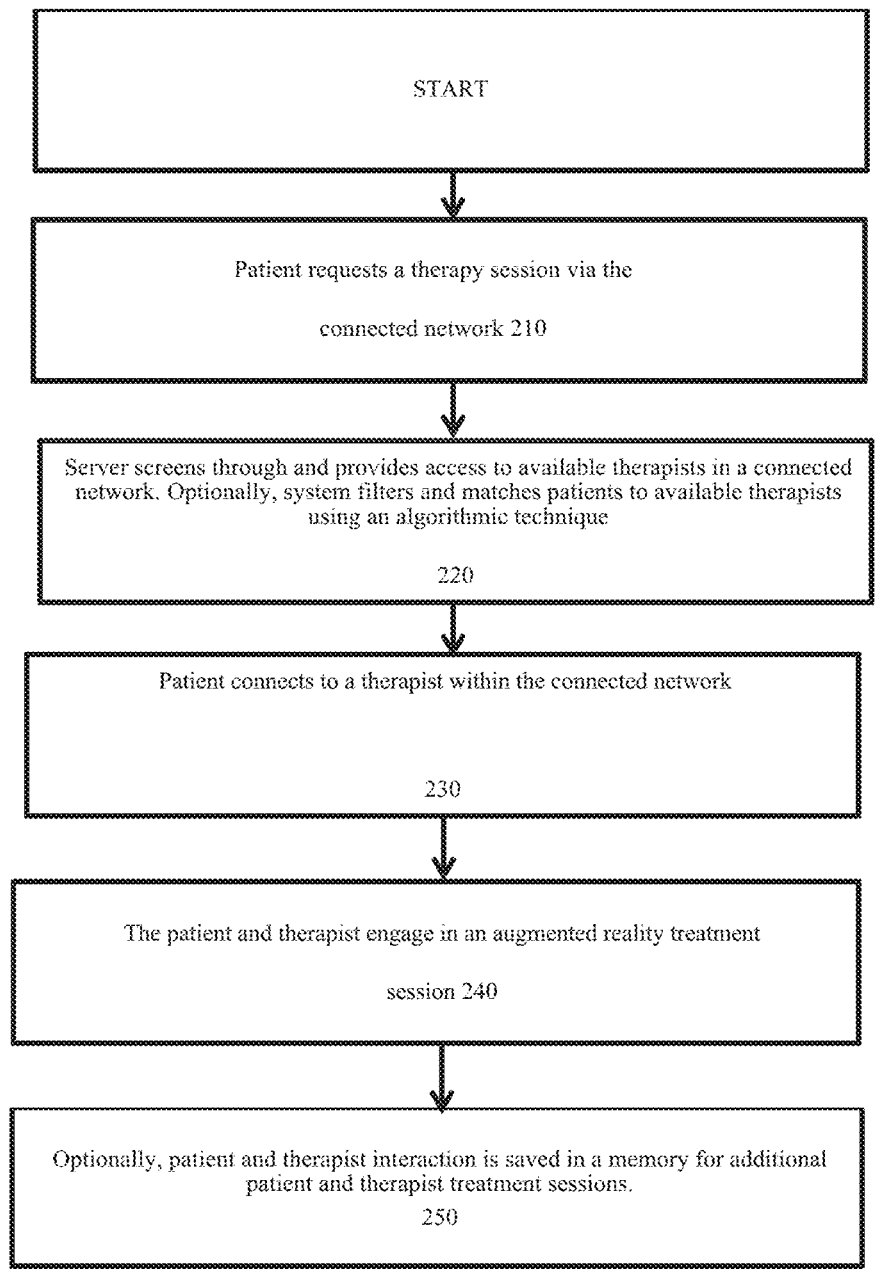
FIG. 8 is a flowchart that illustrates a connected network between patients and therapists.

FIG. 8 is a flowchart that illustrates a connected network between patients and therapists. FIG. 8 involves step 210 where a patient requests a therapy session via the connected network. Step 220 involves the server screens through and provides access to available therapists in a connected network. Optionally, system filters and matches patients to available therapists using an algorithmic technique. Step 230 involves the patient being connected to a therapist within the connected network. Step 240 involves the patient and therapist engage in an augmented reality treatment session. Step 250 involves the patient and therapist interaction is saved in a memory for additional patient and therapist treatment sessions.

Figure 9:
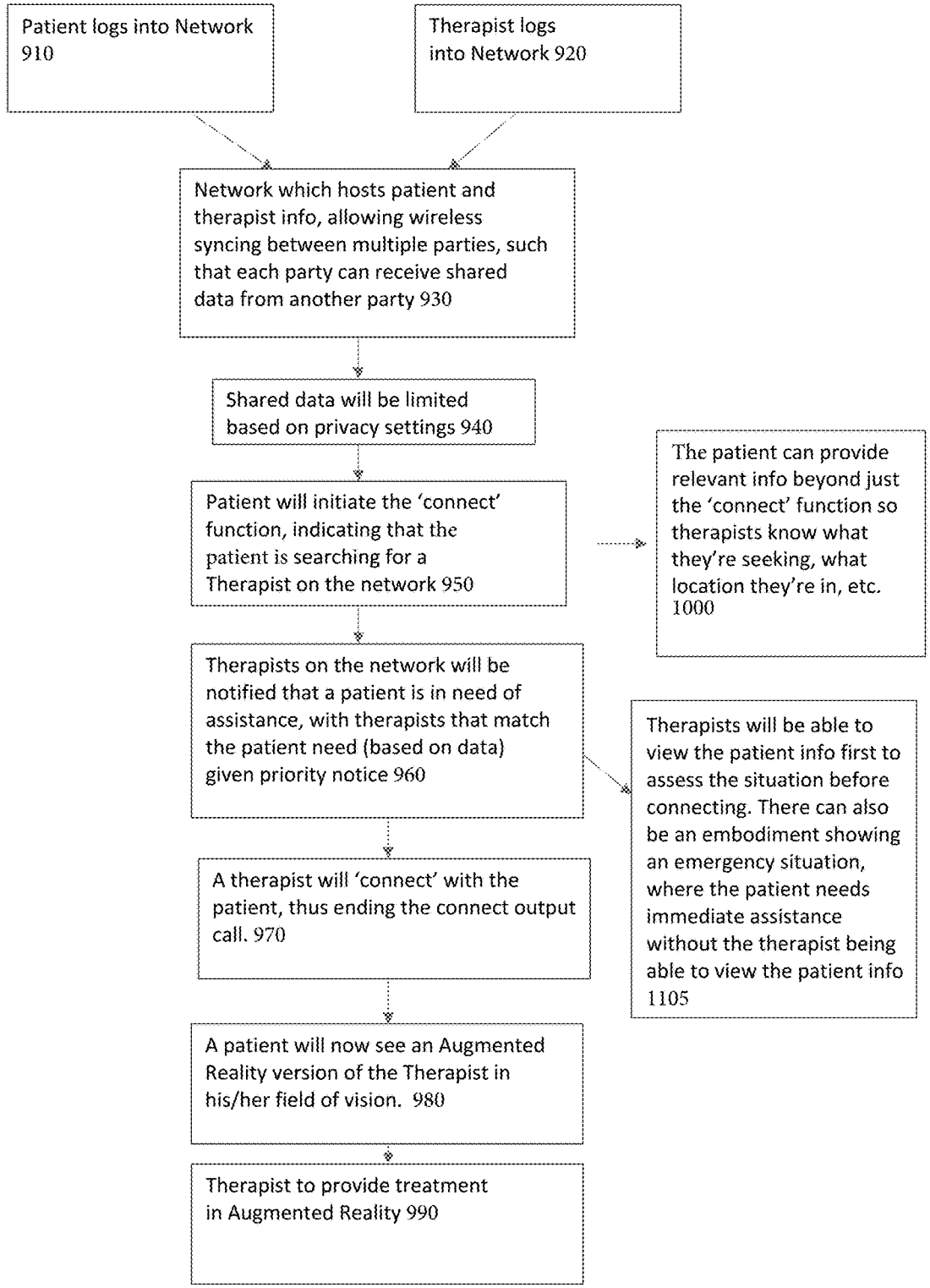
FIG. 9 is another flowchart that illustrates a connected network between patients and therapists

FIG. 9 is another flowchart that illustrates a connected network between patients and therapists. FIG. 9 involves both a patient 910 and therapist 920 logging into a network. Step 930 involves a network, such as a network hosted by a server, which hosts patient and therapist info, allowing wireless syncing between multiple parties, such that each party can receive shared data from another party 930. Step 940 involves shared data will be limited based on privacy settings. Step 950 involves a patient will initiate the 'connect' function, indicating that they're searching for a Therapist on the network. Step 960 involves therapists on the network will be notified that a patient is in need of assistance, with therapists that match the patient need (based on data) given priority notice. Step 970 involves a therapist will 'connect' with the patient, thus ending the connect output call. Step 980 involves a patient will now see an Augmented Reality version of the Therapist in his/her field of vision. Step 990 involves a therapist to provide treatment in Augmented Reality.

In certain embodiments, the patient can provide relevant info beyond just the 'connect' function so therapists know what they're seeking, what location they're in (1000). In certain embodiments, therapists will be able to view the patient info first to assess the situation before connecting. There can also be an embodiment showing an emergency situation, where the patient needs immediate assistance without the therapist being able to view the patient info.

Additional Embodiments of the Invention

Other objects of the invention are achieved by providing a method for treating a patient using augmented reality (AR), the method comprising: administering an augmented reality version of a licensed healthcare professional/therapist within a field of view of the patient.

In certain embodiments, the augmented reality version of a licensed healthcare professional/therapist provides a therapy treatment to the patient.

In certain embodiments, the augmented reality version of a licensed healthcare professional and/or therapist further includes, but is not limited to computer generated inputs, or sensory input such as sound, video, graphics, haptics or GPS data.

In certain embodiments, the augmented reality version of a licensed healthcare professional/therapist decreases the likelihood that the patient will dropout and cease therapy.

In certain embodiments, the licensed healthcare professional/therapist is actively treating the patient while the patient is receiving a therapy.

In certain embodiments, the patient receives the therapy treatment outside of an office of the licensed healthcare professional/therapist.

In certain embodiments, the patient receives the therapy treatment at home.

In certain embodiments, the patient is suffering from a mental health and developmental disorder.

Other objects of the invention are achieved by providing a process for mental health and developmental disorder patients to seek treatment outside of the office in both public and private spaces, thus encouraging higher rates of therapy usage as well as higher success rates of treatment completion.

Other objects of the invention are achieved by providing a system for treating a patient using augmented reality (AR), the system comprising: a processor; software executing on the processor that provides an augmented reality version of a licensed healthcare professional/therapist within a field of view of the patient.

Computer Hardware

In certain embodiments of the device, the AR device includes a computer memory, a processor, a headset. In certain embodiments, the AR device is part of a larger system that includes a camera and a mobile device to stream the virtual therapist to the AR device.

Hardware components for augmented reality are: processor, display, sensors and input devices. Other components include a camera and MEMS sensors such as accelerometer, GPS, and solid state compass.

AR displays can be rendered on devices resembling eyeglasses or lenses, including contact lenses.

Various technologies are used in augmented reality rendering, including optical projection systems, monitors, handheld devices, and display systems worn on the human body.

Exemplary Embodiments Described Above

It should be understood that this description is not intended to limit the embodiments. On the contrary, the embodiments are intended to cover alternatives, modifications, and equivalents, which are included in the spirit and scope of the embodiments as defined by the appended claims. Further, in the detailed description of the embodiments, numerous specific details are set forth to provide a comprehensive understanding of the claimed embodiments. However, one skilled in the art would understand that various embodiments can be practiced without such specific details.

Although the features and elements of aspects of the embodiments are described being in particular combinations, each feature or element can be used alone, without the other features and elements of the embodiments, or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and can include other examples that occur to those skilled in the art. Such other examples are intended to be within the scope of the claims.

The above-described embodiments are intended to be illustrative in all respects, rather than restrictive, of the embodiments. Thus, the embodiments are capable of many variations in detailed implementation that can be derived from the description contained herein by a person skilled in the art. No element, act, or instruction used in the description of the present application should be construed as critical or essential to the embodiments unless explicitly described as such. Also, as used herein, the article "a" is intended to include one or more items.

All United States patents and applications, foreign patents, and publications discussed above are hereby incorporated herein by reference in their entireties.

What is claimed is:

1. A computer-implemented method for treating a patient suffering from a mental health, behavioral health, or developmental disorder using augmented reality (AR), the method comprising:
    providing an AR device to a patient, the AR device having at least one processor;
    creating, via software executing on a processor, an AR field of view;
    receiving therapist information relating to a plurality of therapists and creating an AR therapist avatar for each of said therapists, said therapist information comprising at least each of said therapists' treatment abilities;
    receiving patient information relating to said patient, said patient information comprising at least said patient's location and desired treatment, wherein said patient information may optionally further comprise a showing of an emergency situation;
    initiating a connect function indicated by said patient once said patient is in need of assistance;
    after said initiating step, if said patient information comprises said showing of an emergency situation, then immediately selecting one of said therapists to connect to said patient without allowing said selected one of said therapists to view said patient information;
    after said initiating step, if said patient information does not comprise said showing of an emergency situation, then notifying said therapists that said patient is in need of assistance and sharing said patient information with said therapists;
    after said notifying step, connecting said patient to a first of said therapists who has chosen to connect with said patient;
    overlaying, via software executing on processor, the AR therapist avatar of said first therapist within the AR field of view to create a modified AR field of view; and
    displaying the modified AR field of view on the AR device,
    wherein the AR therapist within the modified AR field of view provides a therapy to said patient to treat the patient suffering from a mental health, behavioral health, or developmental disorder.

2. The computer-implemented method of claim 1, wherein the therapy is personalized to the patient.

3. The computer-implemented method of claim 1, wherein the therapist is a live therapist, a recording of a therapist, or a pre-recording of a therapist.

4. The computer-implemented method of claim 1, wherein the field of view is a live field of view of the patient's current location or an alternative location.

5. The computer-implemented method of claim 4, wherein the alternative location is selected from a group consisting of a beach, a bamboo forest, a mountaintop or other location associated with relaxation.

6. The computer-implemented method of claim 1, wherein the therapist engages in therapy conversation with the patient, specifically related to a mental health, behavioral health, or development disorder.

7. The computer-implemented method of claim 1, wherein the therapist actively treats the patient, such that the patient is able to ask questions to the therapist and have an interactive live conversation with the therapist.

8. The computer-implemented method of claim 1, wherein the augmented reality (AR) device is a headset, glasses wear such as lenses or contact lenses, wearable device, or wearable medical device.

9. The computer-implemented method of claim 1, wherein the AR therapist provides treatment in emergency situations for life saving purposes for the patient or those around the patient.

10. The computer-implemented method of claim 1, wherein the AR therapist is available in remote areas for patients having stress management or mental health management.

11. The computer-implemented method of claim 1, wherein the AR therapist is accessible to the patient for live treatment outside of a hospital system.

12. The computer-implemented method of claim 1, wherein the AR therapist avatar is a projected image of a licensed therapist and is able to treat patients outside of their proximity as well as reduce downtime in-between seeing patients.

13. The computer-implemented method of claim 1, wherein the AR therapist is able to treat patients from the comfort of their own home.

14. The computer-implemented method of claim 1, wherein the method prevents the patient from the social stigma of seeing a live therapist and/or having to go to a hospital or clinical setting to see the therapist.

15. The computer-implemented method of claim 1, wherein the method allows for the patient to have on-demand access to a therapist.

16. An augmented reality (AR) system for treating a patient suffering from a mental health, behavioral health, or developmental disorder, the system comprising:
    a server configured to:
        receive therapist information relating to a plurality of therapists and create an AR therapist avatar for each of said therapists, said therapist information comprising at least each of said therapists' treatment abilities;
        receive patient information relating to said patient, said patient information comprising at least said patient's location and desired treatment, wherein said patient information may optionally further comprise a showing of an emergency situation;
        initiate a connect function indicated by said patient once said patient is in need of assistance;
        after said initiate step, if said patient information comprises said showing of an emergency situation, then immediately select one of said therapists to connect to said patient without allowing said selected one of said therapists to view said patient information
        after said initiate step, if said patient information does not comprise said showing of an emergency situation, then notify said therapists that said patient is in need of assistance and sharing said patient information with said therapists
        after said notify step, connecting said patient to a first of said therapists who has chosen to connect with said patient
    at least one processor; and
    at least one computer-readable storage media storing instructions which, when executed by the at least one processor:
        creates an AR field of view,
        overlays said AR therapist avatar of said first therapist within the AR field of view to create a modified AR field of view, and
        displays modified AR field of view on the AR device, wherein the AR therapist avatar of said first therapist within the modified AR field of view provides a therapy to a patient to treat the patient suffering from a mental health, behavioral health, or developmental disorder.

17. The system of claim 16, wherein the system is either a wearable device or a wearable medical device.

18. The system of claim 17, wherein the system is not wirelessly connected to a computer or mobile phone, and operates within its own standalone system.

19. The system of claim 17, wherein the system is wirelessly connected to a computer or mobile phone.

\* \* \* \* \*